US011850397B2

(12) United States Patent
Dave et al.

(10) Patent No.: US 11,850,397 B2
(45) Date of Patent: Dec. 26, 2023

(54) MEDICAL DEVICE ADAPTIVE CONTROL FOR HOSTILE ENVIRONMENT

(71) Applicant: CareFusion 303, Inc., San Diego, CA (US)

(72) Inventors: Jay Jyotindra Dave, Carlsbad, CA (US); Igor Nesterenko, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 632 days.

(21) Appl. No.: 17/000,225

(22) Filed: Aug. 21, 2020

(65) Prior Publication Data

US 2021/0060243 A1 Mar. 4, 2021

Related U.S. Application Data

(60) Provisional application No. 62/891,869, filed on Aug. 26, 2019.

(51) Int. Cl.
*A61M 5/172* (2006.01)
*G16H 20/17* (2018.01)
(Continued)

(52) U.S. Cl.
CPC ............ *A61M 5/172* (2013.01); *A61M 5/142* (2013.01); *G01D 5/145* (2013.01); *G01J 1/4209* (2013.01); *G01K 3/005* (2013.01); *G01R 31/3647* (2019.01); *G01R 33/07* (2013.01); *G05B 23/0259* (2013.01); *G16H 20/17* (2018.01); *G16H 40/40* (2018.01); *G16H 40/67* (2018.01); *A61M 2205/3317* (2013.01); *A61M 2205/3368* (2013.01); *A61M 2205/50* (2013.01); *A61M 2205/8212* (2013.01)

(58) Field of Classification Search
None
See application file for complete search history.

(56) References Cited

U.S. PATENT DOCUMENTS

2014/0276536 A1 9/2014 Estes
2017/0266378 A1 9/2017 Kamen et al.

FOREIGN PATENT DOCUMENTS

EP 1716878 A1 * 11/2006 ........ A61M 5/14276

OTHER PUBLICATIONS

Written Opinion of the International Preliminary Examining Authority for Application No. PCT/US2020/047839, dated Aug. 25, 2021, 8 pages.

(Continued)

*Primary Examiner* — Manuel A Mendez
(74) *Attorney, Agent, or Firm* — Morgan, Lewis & Bockius LLP

(57) ABSTRACT

A medical device is configured to monitor, using one or more sensors, an environmental condition of a physical environment proximate to a medical device, and to determine when a value representative of the environmental condition exceeds a threshold for safe operation of the medical device with regard to care of a patient. Responsive to the value exceeding the threshold, an operation mode of the medical device is automatically switched from a first mode currently programmed for the care of the patient to a second mode, the second mode using different parameters than the first mode to control the medical device.

19 Claims, 4 Drawing Sheets

(51) Int. Cl.
| | |
|---|---|
| *G16H 40/67* | (2018.01) |
| *G16H 40/40* | (2018.01) |
| *G01R 31/36* | (2020.01) |
| *A61M 5/142* | (2006.01) |
| *G01D 5/14* | (2006.01) |
| *G01J 1/42* | (2006.01) |
| *G01K 3/00* | (2006.01) |
| *G01R 33/07* | (2006.01) |
| *G05B 23/02* | (2006.01) |

(56) References Cited

OTHER PUBLICATIONS

International Preliminary Report on Patentability from the International Preliminary Examining Authority for Application No. PCT/US2020/047839, dated Dec. 8, 2021, 9 pages.
International Search Report and Written Opinion for Application No. PCT/US2020/047839, dated Feb. 1, 2021, 18 pages.
Invitation to Pay Additional Fees and Partial International Search Report for Application No. PCT/US2020/047839, dated Dec. 2, 2020, 14 pages.
Australian Office Action for Application No. 2020337414, dated Jun. 29, 2023, 3 pages.

* cited by examiner

MEDICAL DEVICE ADAPTIVE CONTROL FOR HOSTILE ENVIRONMENT

CROSS REFERENCE TO RELATED APPLICATIONS

This application claims the benefit as a nonprovisional of U.S. Application Ser. No. 62/891,869, entitled "MEDICAL DEVICE ADAPTIVE CONTROL FOR HOSTILE ENVIRONMENT," filed on Aug. 26, 2019, the entirety of which is incorporated herein by reference.

TECHNICAL FIELD

This application relates generally to maintaining the safety and performance of medical devices throughout a healthcare organization.

BACKGROUND

Temperature, atmospheric pressure, electromagnetic waves, certain radio frequencies, and other environmental factors may influence the operation of a medical device. For example, these and other environmental conditions can interfere with the desired operation of sensitive circuitry within a medical device such as an infusion pump. These factors may have an even larger influence on medications provided by a medical device. Failure of a medical device or a medication increases the health risk to the patients of a healthcare facility.

SUMMARY

According to various aspects, the subject technology provides a medical device configured to monitor, using one or more sensors, an environmental condition of a physical environment proximate to a medical device, and to determine when a value representative of the environmental condition exceeds a threshold for safe operation of the medical device with regard to care of a patient. Responsive to the value exceeding the threshold, an operation mode of the medical device is automatically switched from a first mode currently programmed for the care of the patient to a second mode, the second mode using different parameters than the first mode to control the medical device.

According to various aspects, a machine-implemented method includes monitoring, using one or more sensors, an environmental condition of a physical environment proximate to a medical device; determining a value representative of the environmental condition exceeds a threshold for safe operation of the medical device with regard to care of a patient; and automatically switching, responsive to the value exceeding the threshold, an operation mode of the medical device from a first mode currently programmed for the care of the patient to a second mode, the second mode using different parameters than the first mode to control the medical device. Switching the operation mode of the medical device may include disabling use of a first sensor measurement, wherein the first mode comprises determining an operation performance of a hardware device based on the first sensor measurement, and the second mode comprises determining the operation performance based on a software algorithm that does not use the first sensor measurement. Other aspects include corresponding systems, apparatuses, and computer program products for implementation of the machine-implemented method.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

The subject technology includes a system that utilizes sensors and/or other operational features of a medical device (e.g., such as an infusion pump) to collect signals and to, based on those signals, detect hostile environments that may interfere with operational conditions of the device. According to some implementations, the medical device may suggest corrective action(s) to address the interference. As used herein, a "hostile" environment or condition may refer to an environment or condition that can impact the medical device (e.g., negatively or unexpectedly), cause the medical device to experience a hostile event, affect a current mode of operation of the medical device, or affect the ability of certain hardware components of the medical device to operate within an expected range or tolerance. A hostile event may not necessarily be negative or unexpected, but the event may require adjustment to the medical device to ensure safe operation.

For example, some care areas, such as MRI, may include magnetic fields which can impact medical device functions.

These strong magnetic fields may impact or even be disruptive to certain circuits and/or sensors of a medical device including, for example, a Hall sensor implemented by the device. In this regard, disruption of the Hall sensor function may cause a diminished capability, or even a failure, of a medical device's volume sensing feature, which relies upon the Hall sensor for accurate readings. According to various aspects of the subject technology, a medical device is configured to, when there is a potential for circuitry of the medical device to be impacted by conditions within a hostile environment, adjust or change operational modes, for example, to rely on software functions (e.g., a software based volume sensing) rather than the more accurate sensing that the circuit may provide (e.g., Hall sensing).

Figure 1:
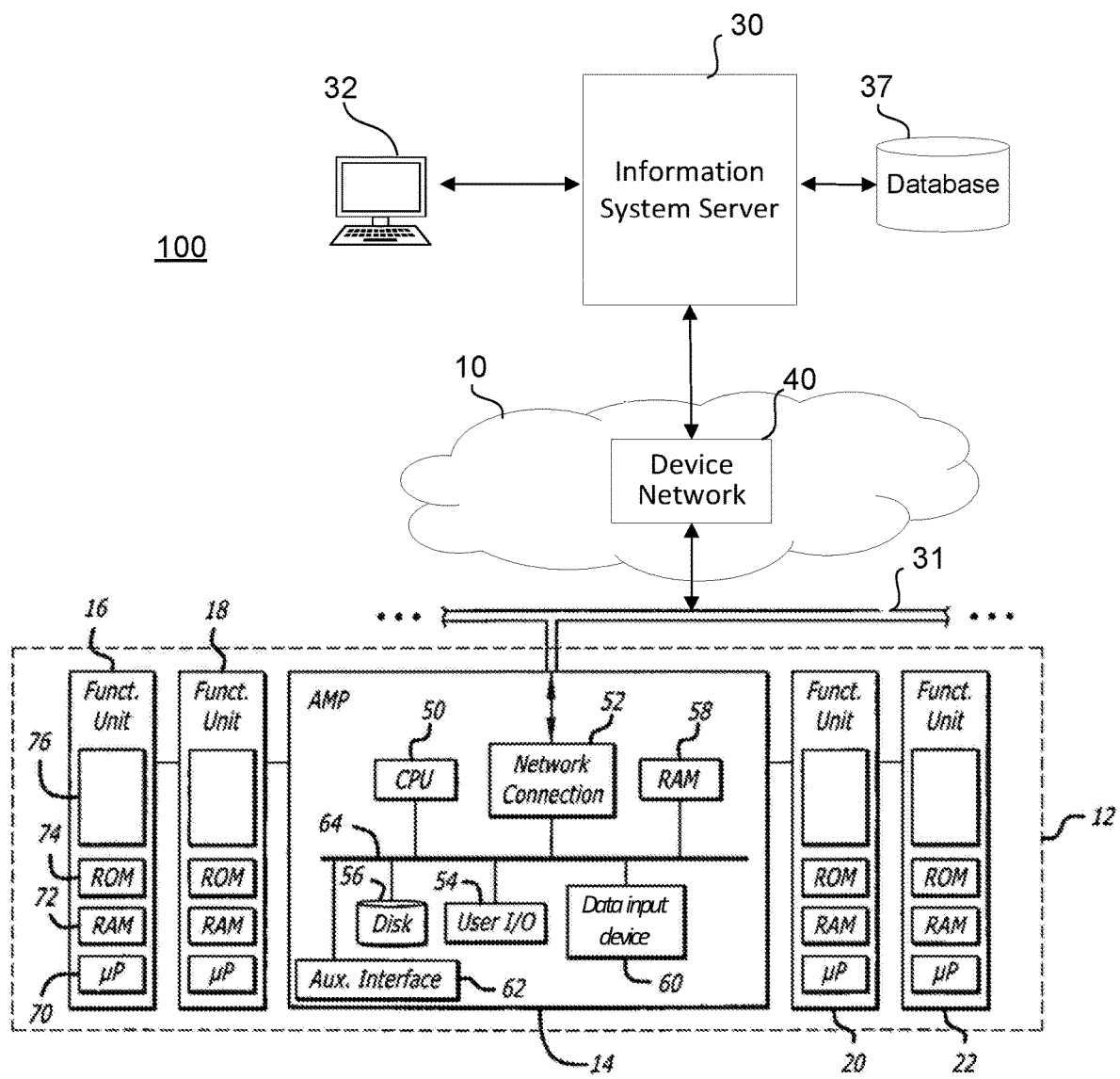
FIG. 1 depicts an example of an institutional patient care system of a healthcare organization, according to aspects of the subject technology.

FIG. 1 depicts an example of an institutional patient care system 100 of a healthcare organization, according to aspects of the subject technology. In FIG. 1, a patient care device (or "medical device" generally) 12 is connected to a hospital network 10. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each element 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 40 by which patient care devices 12 (and other devices) communicate in accordance with normal operations.

Additionally, institutional patient care system 100 may incorporate a separate information system server 30, the function of which will be described in more detail below. Moreover, although the information system server 30 is shown as a separate server, the functions and programming of the information system server 30 may be incorporated into another computer, if such is desired by engineers designing the institution's information system. Institutional patient care system 100 may further include one or multiple device terminals 32 for connecting and communicating with information system server 30. Device terminals 32 may include personal computers, personal data assistances, mobile devices such as laptops, tablet computers, augmented reality devices, or smartphones, configured with software for communications with information system server 30 via network 10.

Patient care device 12 comprises a system for providing patient care, such as that described in U.S. Pat. No. 5,713,856 to Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 16, 18, 20, 22. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 18, 20 and/or 22 may be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 may include module-specific components 76, a microprocessor 70, a volatile memory 72 and a nonvolatile memory 74 for storing information. It should be noted that while four functional modules are shown in FIG. 1, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 16.

While each functional module may be capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Patient care device 12 is capable of operating in several different modes, or personalities, with each personality defined by a configuration database. The configuration database may be a database 56 internal to patient care device, or an external database 37. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within patient care device 12 itself.

Figure 2:
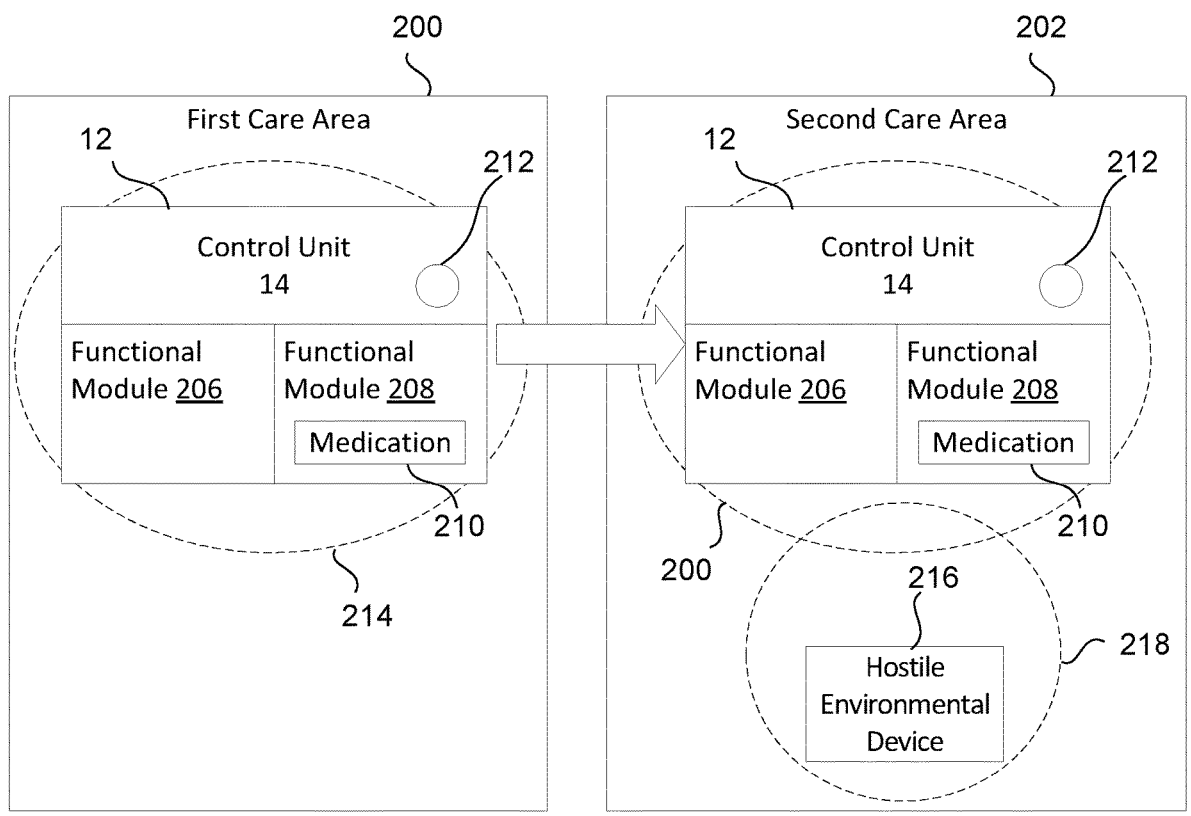
FIG. 2 depicts an example of a medical device moving between patient care areas, and detecting a hostile environmental condition, in accordance with aspects of the subject technology.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication FIG. 2 depicts an example a medical device moving between a first care area 200 and a second care area 202, and detecting a hostile environmental condition, in accordance with aspects of the subject technology. As shown, a medical device 12 may include a control unit 204 and one or more functional modules (e.g., functional modules 16, 18, 20, 22), including a first functional module 206 and a second functional module 208. The second functional module 208 is depicted as including a medication 210. In some implementations, medical device 12 may be a dispensing device configured to, on authorizing a clinician, dispense the medication 210 for care of the patient. In some implementations, medical device 12 may be an infusion device configured to administer the medication 210 to the patient (e.g., intravenously by way of a connected infusion set). Control unit may include one or more processors such as to be configured to interface with the functional units and to control and provide power to the functional units when the functional units are connected to the control unit.

According to various aspects of the subject technology, medical device 12 may include one or more sensors 212 configured to detect respective environmental conditions.

Medical device 12 may be configured to monitor, using sensor(s) 212, an environmental condition of a physical environment proximate to a medical device. In this regard, sensor(s) 212 may include a thermistor, radio frequency (RF) receiver, magnetometer, light sensor, and the like. For example, a sensor 212 may be configured to detect ambient temperature, radiant temperature, an amount of light, acoustical transmissions (sound), a magnetic field and its strength. Sensor(s) 212 may have a range 214.

Medical device 12 may include circuitry that causes sensor(s) 212 to obtain a measurement value representative of the environmental condition. Sensor(s) 212 may measure the environmental condition periodically, or upon certain trigger conditions. One example trigger condition may include the medical device 12 detecting that it has moved to a new location. Medical device 12 may query an internal database 56 or a server 30 and/or a corresponding external database 37 based on its known coordinates (e.g., GPS) or based on connecting to a new WiFi system to determine whether its new physical environment includes a (potentially) hostile environmental device 216, and receive an indication of the trigger condition on determining the (potential) presence of device 216. Device 216 may include various electrical or mechanical equipment emitting an energy field 218 that may be disruptive to circuitry of medical device 12. Disruptive energy fields include, for example, magnetic fields (e.g., from an MRI machine), predetermined radio frequency, heat, cold, air, vibrations, and sound.

When receiving a measurement value, medical device 12 may determine when the value exceeds a threshold for safe operation of the medical device with regard to care of a patient. Various thresholds may, for example, be stored in a database and indexed by one or more indexes including care area, patient medical condition, time of day, and the like. Responsive to the value exceeding the threshold, an operation mode of the medical device may be automatically switched from a first mode currently programmed for the care of the patient to a second mode. According to various aspects, the second mode may utilize different parameters than the first mode to control the medical device. For example, a first mode may operate a pump according to a first flow rate, and a second mode may operate the pump according to a second, lower flow rate. A parameter of a first mode may activate a functional module, and parameter of a second mode may deactivate the functional module.

Computer program code for carrying out operations of the subject technology may be written in an object oriented programming language such as, for example, JAVA®, Smalltalk, or C++. However, the computer program code for carrying out operations of the subject technology may also be written in conventional procedural programming languages, such as the "C" programming language, in an interpreted scripting language, such as Perl, or in a functional (or fourth generation) programming language such as Lisp, SML, Forth, or the like. The software may also be written to be compatible with HLA-7 requirements.

According to various implementations, a medical device 12 may include and/or utilize one or more on-board sensors 212 such as a magnetometer, temperature sensor, acoustic sensor, or light sensor, that are configured to measure environmental conditions and assign values representative of the environmental conditions. The medical device 12 may include circuitry and/or software that monitors the measurements and/or values received from each of these sensors. When a medical device (or its network circuitry) 12 detects one of these measurements and/or values satisfies (e.g., exceeds) a predetermined threshold, the medical device may be triggered to automatically adjust or change modes.

According to various implementations, a medication 210 administered or otherwise provided by a medical device may be sensitive to certain environmental conditions. Accordingly, the medical device 12 may be configured to monitor the environmental conditions surrounding the medical device 12 using one or more sensors 212, as described previously, for conditions that could adversely affect the medication 210 or a delivery of the medication 210. The medical device 12 may further be configured to automatically assign predetermined thresholds for a measured environmental condition (e.g., temperature or amount of light) based on the medication 210 it is providing. In some implementations, the predetermined threshold may be based on a predetermined amount that the measured environmental condition reduces a half-life of medication.

The thresholds or threshold ranges may be stored, for example, in a lookup table or databased indexed by the type(s) of medication(s) and the particular environmental condition(s) being measured. For example, a drug dispensing device may automatically measure temperature values within each cabinet containing medication. When the temperature becomes out of a predetermined safe range of temperature in which the medication should be stored the device may automatically adjust or change modes. Similarly, an infusion device may, on being programmed to administer a given medication, lookup safe ranges for environmental conditions such as temperature and light for the given medication, and begin monitoring environmental conditions proximate to the device to ensure these ranges are satisfied. When a medical device (or its network circuitry) detects one of these measurements and/or values satisfies (e.g., exceeds) a predetermined threshold, the medical device may be triggered to automatically adjust or change modes.

According to various implementations, adjusting or changing a mode of operation may include taking a correct action. A corrective action may include displaying an alert on the medical device and/or sounding an audible alert. A corrective action may include stopping an ongoing administration of a medication or locking the device from administering or providing further medications until the alert has been acknowledged. Acknowledgement may include identifying a clinician authorized to the medical device by way of the clinician scanning a badge, and the clinician manually dismissing the alert by way of a manual input at the medical device or by way of a computing device connected to the medical device (e.g., over a network).

In one example, an infusion pump may be programmed to administer a medication to a patient. The pump may include a temperature sensor and/or a light sensor proximate to a location at which the medication is stored for delivery by the pump. The infusion pump may include a radiant temperature sensor to detect radiant energy indicative of heat emitted from the medication, may include a thermistor which reads an ambient temperature of the room or a temperature of the line used to deliver the medication. During the administration of the medication to the patient, the pump may monitor (using the sensors) environmental conditions surrounding the pump, including a temperature or an amount of light. Upon detecting that the amount of light exceeded a threshold amount of light for a threshold period of time, and/or upon detecting that the temperature exceeded a threshold temperature for a threshold period of time, the pump may issue an alert and/or halt administration of the medication to the patient.

In another example, an infusion pump may be utilize a Hall sensor to measure stroke volume or to detect air bubbles in the medication administration line. For example, this sensor may be used to calculate a stroke rate and a corresponding rate of pumping, and then a processor may make adjustments to the pump's motor speed to correct for set point deviations. The sensor may be used to detect strokes so that a timed history of the number of pump strokes completed may be maintained and used to calculate flow rate and total dispensed volume. The infusion pump may further include a magnetometer configured to measure magnetism, including the direction, strength, or relative change of a magnetic field, at a location proximate to the infusion pump. Upon the magnetometer detecting a magnetic field (e.g., strength or change) above a threshold level indicative of causing an impact to Hall sensor measurements, a processor associated with the infusion pump (or magnetometer) may automatically disable the Hall sensor and switch the calculation of pumping rate, stroke rate, flow rate and volume to be made by software.

In some implementations, the software calculations may not be as accurate as calculations performed by circuitry that was deactivated due to a given environmental condition. The medical device may be configured with a predetermined acceptable accuracy (e.g., 5%) which, if exceed, may trigger the medical device a make the mode change or other adjustment in operation. For example, responsive to detecting an adverse environmental condition an infusion pump may switch to using a software calculation, but then may switch medication administration or other operating parameters if the pump determines that the software calculation cannot maintain the predetermined acceptable accuracy. In some implementations, the current settings of the medical device may have a further impact on this accuracy, and these settings may be adjusted to compensate for a degree of potential error. For example, when a temperature or Hall sensor of an infusion device is disabled due to an environmental condition, a degree of potential error (or accuracy) in the software calculation of a flow rate may further be determined based on the flow rate itself. During critical medication administration, the infusion pump may be configured to adjust the flow rate by a minimum amount necessary to maintain the acceptable amount of error.

Many medical devices may be battery operated, so that the devices may maintain operations in the event of a power outage or when moving between care areas. The battery unit of a medical device may provide power to, for example, one or more processors responsible for operations, a pumping mechanism (e.g., in the case of an infusion pump), an electronic lock (e.g., in the case of a dispensing device), or network circuitry. The battery unit may also be responsible for providing power to subordinate or secondary devices connected to the medical device. For example, a battery unit of an infusion device may provide power to one or more connected functional modules that each include an infusion pump, a syringe pump, a PCA pump, an epidural pump, an enteral pump, a blood pressure monitor, a pulse oximeter, an EKG monitor, an EEG monitor, a heart rate monitor, an intracranial pressure monitor, or the like.

In some implementations, a medical device 12 may utilize one or more temperature sensors to detect an ambient temperature in a room in which the device is located, or to detect an internal temperature of the device itself or its battery or battery compartment. One or more temperature measurements may be obtained using the temperature sensor (s) 212 and used to determined whether to adjust a power allotment to the various systems of the medical device 12, including to any connected functional modules 16, 18, 20, 22. Higher operating temperatures may tend to shorten a battery's capacity and life. A medical device 12 may obtain data regarding its battery's expected capacity or life based on various factors including current operating temperature, depth of discharge, rate of discharge, and previously known capacities under similar conditions. If the medical device determines that the battery's expected capacity is lower than a predetermined threshold for maintaining current operations for a predetermined time period, the medical device may enter a power saving mode and begin to shut down or reduce operation of non-essential systems. Functional units and or medical device features may be determined to be essential or non-essential depending on various factors, including care area 200, 202, status of the patient, time to next charge, etc. In some examples, network connectivity may be identified as a non-essential system. In other examples, network connectivity may be identified as an essential system. Audible alarms may be identified as essential in high traffic noisy critical care areas such as an intensive care unit, but not when the device is identified as being in transit from one area to another.

In one example, a control unit 14 associated with an infusion pump configured according to the subject technology may monitor temperature, and determine that a battery does not have enough capacity to operate the pumping mechanism(s) at a currently set flow rate for a period of time required for medicating the patient prior to receiving a next charge. The predetermined period of time may be a default period of time for operating during a power loss, or may be set by the user via a configuration menu displayed on a display screen of the device, or may be provided to the infusion pump (or other medical device) by the hospital information server in connection with instructions for relocating the device from a first care unit to a second care unit. In response to determining that the battery does not have the capacity to maintain the current pumping load, the control unit may automatically enter a power saving mode and reduce the pumping rate to a level such that that the pumping mechanism may continue pumping throughout the required period of time. In some implementations, the control unit may shut down non-essential functioning units (such as a blood pressure device or pulse oximeter) while maintaining operation of essential functional units such as the pumping mechanism responsible for pumping a life-supporting medication. The control unit may also lock out the potential for module connectivity such that additional functional modules may not be attached while the device is in the power saving mode.

In some implementations, the predetermined threshold for a given environmental condition may be based on certain characteristics of equipment connected to the medical device. For example, different infusion set tubing thicknesses may behave differently under different temperatures; in other words, a thicker tuber may implement a stronger resistance to pumping when in colder environments. In this example, the threshold may be a colder temperature at which the tubing becomes less pliable, and at which the pump should be switched to a more aggressive pumping strength or speed to compensate for the increased pumping resistance.

In some implementations, detection of an environmental condition may be responsive to an error reported by a component of the medical device 12 (or any component or module of the medical device). For example, a control unit 14 of the medical device 12 may detect a Hall sensor error (e.g., a sensor measurement outside an expected measurement range). Responsive to detecting the error an environmental sensor is activated and the control unit receives an environment signal. For example, the medical device 12 may check measurement(s) from a magnetometer, temperature sensor, acoustic sensor, or light sensor to confirm that measurement(s) are within expected ranges. Additionally, the medical device 12 may receive other environmental conditions based on a location of the device (e.g., measured by GPS), a logged in clinician profile, network status, and the like. If the environmental conditions indicate that features of the medical device may be impacted (from the hostile environment) then the medical device may adjust or change modes, as indicated above. In some implementations, the medical device may provide an alert and prompt a user to make or confirm the change. For example, an infusion pump may require a manual confirmation to switch to software flow detection, in which the switch is responsive to user input via a graphical user interface on or associated with the infusion pump. Accordingly, such additional checks on errors may reduce false alerting of pump errors.

Some environmental conditions may cause a medical device 12 to lose network connectivity. For example, some care areas include shielded rooms (such as MRI rooms) that prevent radio and electromagnetic energy from passing through walls. When a medical device 12 (or its network circuitry) detects it has lost network connectivity, the medical device may be triggered to automatically adjust or change modes. In one example, on detecting a loss of network connectivity, the medical device 21 may switch to a manual mode in which it begins using an onboard drug library instead of looking up operating parameters and limits via the network connection.

Some medical devices 12 may include wireless circuitry used to detect other devices within a predetermined proximity or are of the medical device. For example, a medical device 12 may use Bluetooth to connect to other predesignated medical devices in certain environments. The wireless signature broadcast from a first medical device may cause interference with circuitry of a second medical device, or the connection between the devices may impact the ability of the circuitry to operate properly or to its full potential. In this regard, when the second medical device (or its network circuitry) detects the interference or connection to the first device, the second medical device may be triggered to automatically adjust or change modes.

In some implementations, a medical device 12 may be configured to produce audible or visual alerts prior to or when changing modes. In this regard, the medical device, on losing a network connection, may provide on its associated display device an option for mode adjustment. For example, the medical device may prompt a user to select whether to maintain the current mode or adjust the network setting. Options may include selecting from available networks, or selecting a different type of network to use (e.g., Bluetooth or wired instead of WiFi). In some implementations, alerts may be escalated as environmental conditions worsen. For example, as more critical life-supporting systems are impacted different levels of alerts may be produced. A first alert may include a visual alert, while an audible alert may progressively come louder according to different thresholds of impact, with higher impacts leading to network messages being sent to a primary caregiver via the network.

Figure 3:
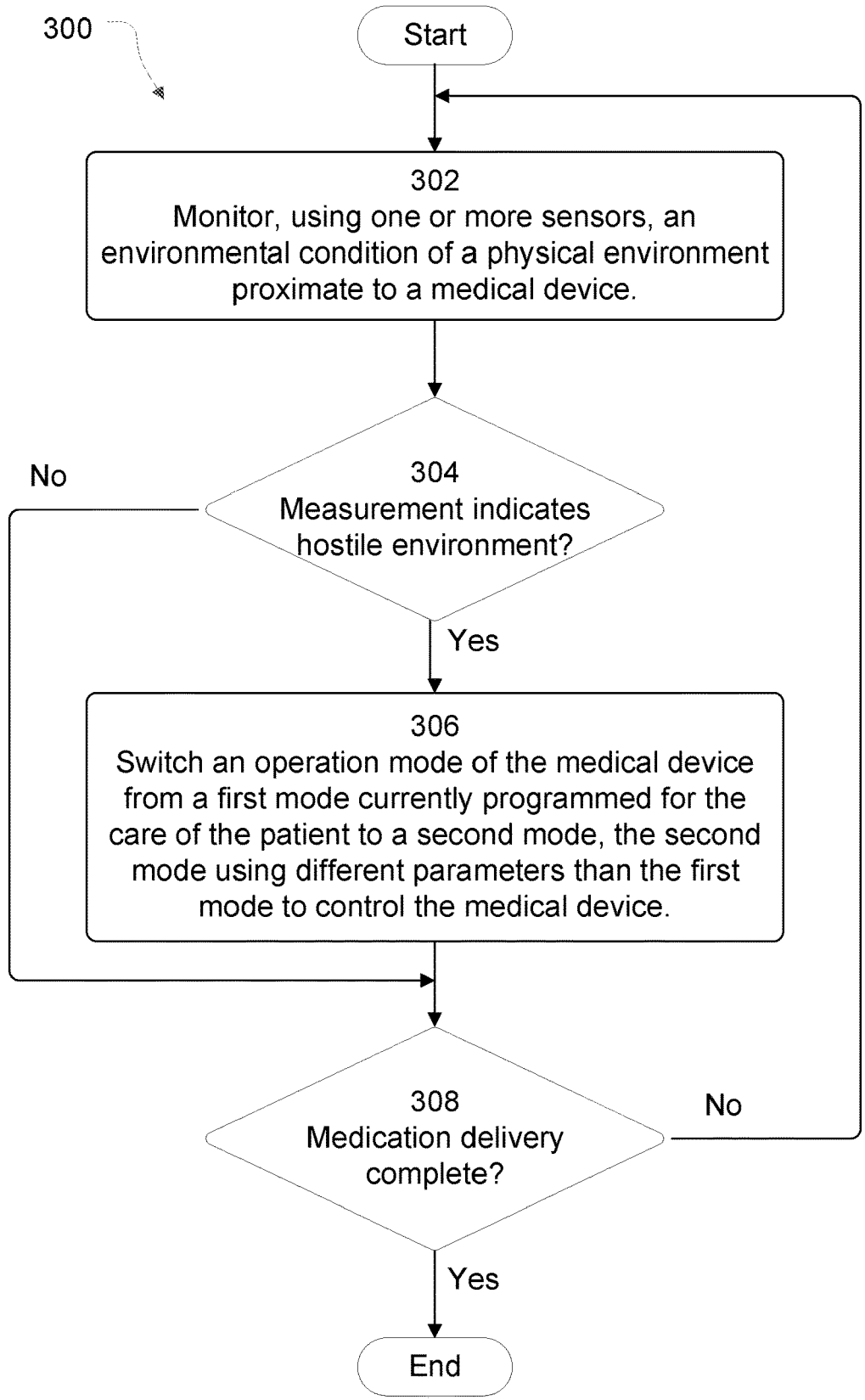
FIG. 3 depicts an example process for automatically adapting control of a medical device responsive to detecting a hostile environment, according to aspects of the subject technology.

FIG. 3 depicts an example process for automatically adapting control of a medical device responsive to detecting a hostile environment, according to aspects of the subject technology. For explanatory purposes, the various blocks of example process 300 are described herein with reference to FIGS. 1 and 2, and the components and/or processes described herein. The one or more of the blocks of process 300 may be implemented, for example, by one or more computing devices including, for example, medical device 12. In some implementations, one or more of the blocks may be implemented based on one or more machine learning algorithms. In some implementations, one or more of the blocks may be implemented apart from other blocks, and by one or more different processors or devices. Further for explanatory purposes, the blocks of example process 300 are described as occurring in serial, or linearly. However, multiple blocks of example process 300 may occur in parallel. In addition, the blocks of example process 300 need not be performed in the order shown and/or one or more of the blocks of example process 300 need not be performed.

In the depicted example, a medical device 12 monitors, using one or more sensors 212, an environmental condition of a physical environment proximate to a medical device (302).

A value representative of the environmental condition is determined to exceed a threshold for safe operation of the medical device with regard to care of a patient (304). For ease of explanation, the relationship to a threshold may be described as "exceeding a threshold" however, additional or alternative relationships to determine whether a value corresponds to a threshold may be included. Furthermore, the threshold may be static value stored in memory or other configuration storage accessible by the medical device or a dynamic threshold value established based on one or more values available to (e.g., programmed operational parameters, default configuration, etc.) or detected by (e.g., temperature, location, speed, orientation, etc.) the medical device.

Responsive to the value exceeding the threshold, an operation mode of the medical device 12 is automatically switched (in real time) from a first mode currently programmed for the care of the patient to a second mode, the second mode using different parameters than the first mode to control the medical device (306). According to various implementations, switching the operation mode of the medical device 12 may include disabling use of a first sensor measurement (or measurements provided by a first sensor). In this regard, the first mode may include determining an operation performance of a hardware device based on the first sensor measurement, and the second mode may include determining the operation performance based on a software algorithm that does not use the first sensor measurement. For example, the medical device 12 may include an infusion device and the one or more sensors 212 may include a magnetometer. In this example, the environmental condition may include a magnetic field, the first sensor measurement may be provided by a Hall sensor, and the operation performance may be associated with a pumping mechanism administering a fluid to the patient.

In some implementations, prior to monitoring the environmental condition, the medical device 12 may include onboard diagnostics to determine during operation that a hardware component of the medical device produced an error exceeding a predetermined error threshold. In these implementations, the monitoring of the environmental condition may be in response to the error exceeding the predetermined error threshold.

In some implementations, the environmental condition includes a temperature, and switching the operation mode of the medical device may include reducing power to a hardware component of the medical device responsive to the temperature exceeding a predetermined temperature threshold. The temperature may be an ambient temperature, an internal temperature of the device (e.g., a compartment), or a temperature of a medication provided by the device.

According to various implementations, the medical device 12 may be an infusion device or a medication dispensing device, and the environmental condition may include a sensed temperature or amount of light that affects a medication provided by the device. A medication dispensing device 12 according to implementations of the subject technology may determine that a medication stored in a compartment of the medication dispensing device has been subjected to the temperature or amount of light for more than a predetermined period of time, and switch the operation mode of the medical device by locking the compartment to prevent a dispense of the medication. An infusion device 12 according to implementations of the subject technology may determine that a medication designated for administration by the medication dispensing device to the patient has been subjected to the temperature or amount of light for more than a predetermined period of time, and switch the operation mode of the medical device by electronically disabling a pumping mechanism of the medical device to prevent the medication from being administered to the patient.

In some implementations, switching the operation mode of a medical device 12 may include entering a power savings mode. The medical device 12 may determine a battery capacity of a battery powering at least the hardware component of the medical device and, based on the measured temperature exceeding the predetermined temperature threshold, determine that the battery capacity is insufficient to power the hardware component for a predetermined period of time. In this regard, switching the operation mode may include adjusting operation parameters used to control at least the hardware component to a reduce a power load of the medical device 12, and the power load may be reduced to a level sufficient for the battery to power the hardware component for the predetermined period of time.

As described previously, the medical device 12 may include a control unit 14 configured to interface with multiple functional units 16, 18, 22, 22 and to control and provide power to a respective functional unit when the functional unit is connected to the control unit. In some implementations, the medical device 12 may determine a battery capacity of a battery powering a the control unit and a plurality of functional units currently connected to the control unit. This determination may be responsive to an increase temperature or may be performed periodically by a battery management system (e.g., circuit and/or software). The medical device may, based on the temperature exceeding the predetermined temperature threshold, determine that the battery capacity is insufficient to power the plurality of functional units for a predetermined period of time, and disable at least one of the plurality of functional units responsive to determining that the battery capacity is insufficient. In some implementations, the medical device may, based on the temperature exceeding the predetermined temperature threshold, determine that the battery capacity is insufficient to power more than the at least one functional unit currently connected to the control unit for a predetermined period of time, and disable the control unit's ability to provide power to any additional functional units other than the at least one functional unit currently connected to the control unit responsive to determining that the battery capacity is insufficient.

Many of the above-described example 300, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 4:
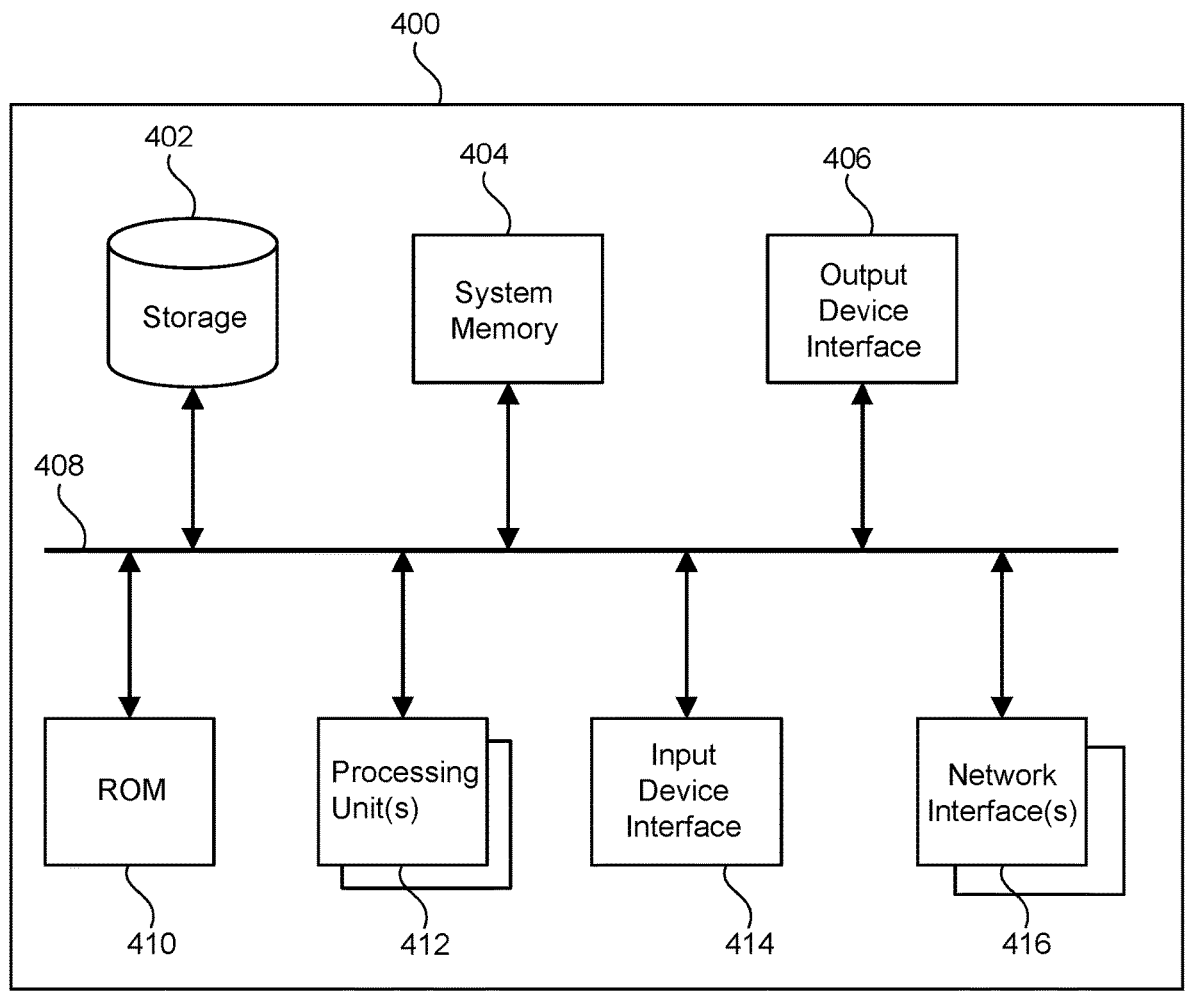
FIG. 4 is a conceptual diagram illustrating an example electronic system for automatically adapting control of a medical device responsive to detecting a hostile environment, according to aspects of the subject technology.

FIG. 4 is a conceptual diagram illustrating an example electronic system 400 for automatically adapting control of a medical device responsive to detecting a hostile environment, according to aspects of the subject technology. Electronic system 400 may be a computing device for execution of software associated with one or more portions or steps of process 400, or components and processes provided by FIGS. 1-3, including but not limited to information system server 30, production server 204, computing hardware within patient care device 12, or terminal device 37. Electronic system 400 may be representative, in combination with the disclosure regarding FIGS. 1-3. In this regard, electronic system 400 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 400 may include various types of computer readable media and interfaces for various other types of computer readable media. In the depicted example, electronic system 400 includes a bus 408, processing unit(s) 412, a system memory 404, a read-only memory (ROM) 410, a permanent storage device 402, an input device interface 614, an output device interface 406, and one or more network interfaces 416. In some implementations, electronic system 400 may include or be integrated with other computing devices or circuitry for operation of the various components and processes previously described.

Bus 408 collectively represents all system, peripheral, and chipset buses that communicatively connect the numerous internal devices of electronic system 400. For instance, bus 408 communicatively connects processing unit(s) 412 with ROM 410, system memory 404, and permanent storage device 402.

From these various memory units, processing unit(s) 412 retrieves instructions to execute and data to process in order to execute the processes of the subject disclosure. The processing unit(s) can be a single processor or a multi-core processor in different implementations.

ROM 410 stores static data and instructions that are needed by processing unit(s) 412 and other modules of the electronic system. Permanent storage device 402, on the other hand, is a read-and-write memory device. This device is a non-volatile memory unit that stores instructions and data even when electronic system 400 is off. Some implementations of the subject disclosure use a mass-storage device (such as a magnetic or optical disk and its corresponding disk drive) as permanent storage device 402.

Other implementations use a removable storage device (such as a floppy disk, flash drive, and its corresponding disk drive) as permanent storage device 402. Like permanent storage device 402, system memory 404 is a read-and-write memory device. However, unlike storage device 402, system memory 404 is a volatile read-and-write memory, such a random access memory. System memory 404 stores some of the instructions and data that the processor needs at runtime. In some implementations, the processes of the subject disclosure are stored in system memory 404, permanent storage device 402, and/or ROM 410. From these various memory units, processing unit(s) 412 retrieves instructions to execute and data to process in order to execute the processes of some implementations.

Bus 408 also connects to input and output device interfaces 414 and 406. Input device interface 414 enables the user to communicate information and select commands to the electronic system. Input devices used with input device interface 414 include, e.g., alphanumeric keyboards and pointing devices (also called "cursor control devices"). Output device interfaces 406 enables, e.g., the display of images generated by the electronic system 400. Output devices used with output device interface 406 include, e.g., printers and display devices, such as cathode ray tubes (CRT) or liquid crystal displays (LCD). Some implementations include devices such as a touchscreen that functions as both input and output devices.

Also, as shown in FIG. 4, bus 408 also couples electronic system 400 to a network (not shown) through network interfaces 416. Network interfaces 416 may include, e.g., a wireless access point (e.g., Bluetooth or WiFi) or radio circuitry for connecting to a wireless access point. Network interfaces 416 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 400 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method, comprising: monitoring, using one or more sensors, an environmental condition of a physical environment proximate to a medical device determining a value representative of the environmental condition exceeds a threshold for safe operation of the medical device with regard to care of a patient; and automatically switching, responsive to the value exceeding the threshold, an operation mode of the medical device from a first mode currently programmed for the care of the patient to a second mode, the second mode using different parameters than the first mode to control the medical device.

Clause 2. The method of Clause 1, wherein switching the operation mode of the medical device comprises disabling use of a first sensor measurement, wherein the first mode comprises determining an operation performance of a hardware device based on the first sensor measurement, and the second mode comprises determining the operation performance based on a software algorithm that does not use the first sensor measurement.

Clause 3. The method of Clause 2, wherein the medical device comprises an infusion device and the one or more sensors comprises a magnetometer, the environmental condition comprising a magnetic field, and wherein the first sensor measurement is provided by a Hall sensor, and the operation performance is associated with a pumping mechanism administering a fluid to the patient.

Clause 4. The method of Clause 1, further comprising: determining, prior to monitoring the environmental condition, a hardware component of the medical device produced an error exceeding a predetermined error threshold, wherein the monitoring of the environmental condition is in response to the error exceeding the predetermined error threshold.

Clause 5. The method of Clause 1, wherein the environmental condition comprises a temperature, and switching the operation mode of the medical device comprises reducing power to a hardware component of the medical device responsive to the temperature exceeding a predetermined temperature threshold.

Clause 6. The method of Clause 5, further comprising: determining a battery capacity of a battery powering at least the hardware component of the medical device; and determining, based on the temperature exceeding the predetermined temperature threshold, that the battery capacity is insufficient to power the hardware component for a predetermined period of time, wherein switching the operation mode comprises adjusting operation parameters used to control at least the hardware component to a reduce a power load of the medical device, and wherein the power load is reduced to a level sufficient for the battery to power the hardware component for the predetermined period of time.

Clause 7. The method of Clause 5, wherein the medical device comprises a control unit configured to interface with multiple functional units and to control and provide power to a respective functional unit when the functional unit is connected to the control unit, and wherein the method further comprises: determining a battery capacity of a battery powering a the control unit and a plurality of functional units currently connected to the control unit; and determining, based on the temperature exceeding the predetermined temperature threshold, that the battery capacity is insufficient to power the plurality of functional units for a predetermined period of time; disabling, responsive to determining that the battery capacity is insufficient, at least one of the plurality of functional units.

Clause 8. The method of Clause 5, wherein the medical device comprises a control unit configured to interface with multiple functional units and to control and provide power to a respective functional unit when the functional unit is connected to the control unit, and wherein the method further comprises: determining a battery capacity of a battery powering a the control unit and at least one functional unit currently connected to the control unit; determining, based on the temperature exceeding the predetermined temperature threshold, that the battery capacity is insufficient to power more than the at least one functional unit currently connected to the control unit for a predetermined period of time; and disabling, responsive to determining that the battery capacity is insufficient, the control unit's ability to provide power to any additional functional units other than the at least one functional unit currently connected to the control unit.

Clause 9. The method of Clause 1, wherein the medical device is a medication dispensing device and the environmental condition comprises a temperature or amount of light, the method further comprising: determining that a medication stored in a compartment of the medication dispensing device has been subjected to the temperature or amount of light for more than a predetermined period of time; and switching the operation mode of the medical device by locking the compartment to prevent a dispense of the medication.

Clause 10. The method of Clause 1, wherein the medical device is an infusion device and the environmental condition comprises a temperature or amount of light, the method further comprising: determining that a medication designated for administration by the medication dispensing device to the patient has been subjected to the temperature or amount of light for more than a predetermined period of time; and switching the operation mode of the medical device by electronically disabling a pumping mechanism of the medical device to prevent the medication from being administered to the patient.

Clause 11. A medical device, comprising: one or more processors; and memory including instructions that, when executed by the one or more processors, cause the medical device to: monitor, using one or more sensors, an environmental condition of a physical environment proximate to the medical device; determine a value representative of the environmental condition exceeds a threshold for safe operation of the medical device with regard to care of a patient; and automatically switch, responsive to the value exceeding the threshold, an operation mode of the medical device from a first mode currently programmed for the care of the patient to a second mode, the second mode using different parameters than the first mode to control the medical device.

Clause 12. The medical device of Clause 11, wherein switching the operation mode of the medical device comprises disabling use of a first sensor measurement, wherein the first mode comprises determining an operation performance of a hardware device based on the first sensor measurement, and the second mode comprises determining the operation performance based on a software algorithm that does not use the first sensor measurement.

Clause 13. The medical device of Clause 12, wherein the medical device comprises an infusion device and the one or more sensors comprises a magnetometer, the environmental condition comprising a magnetic field, and wherein the first sensor measurement is provided by a Hall sensor, and the operation performance is associated with a pumping mechanism administering a fluid to the patient.

Clause 14. The medical device of Clause 11, wherein the instructions, when executed by the one or more processors, further cause the medical device to: determine, prior to monitoring the environmental condition, a hardware component of the medical device produced an error exceeding a predetermined error threshold, wherein the monitoring of the environmental condition is in response to the error exceeding the predetermined error threshold.

Clause 15. The medical device of Clause 11, wherein the environmental condition comprises a temperature, and switching the operation mode of the medical device comprises reducing power to a hardware component of the medical device responsive to the temperature exceeding a predetermined temperature threshold.

Clause 16. The medical device of Clause 15, wherein the instructions, when executed by the one or more processors, further cause the medical device to: determine a battery capacity of a battery powering at least the hardware component of the medical device; and determine, based on the temperature exceeding the predetermined temperature threshold, that the battery capacity is insufficient to power the hardware component for a predetermined period of time, wherein switching the operation mode comprises adjusting operation parameters used to control at least the hardware component to a reduce a power load of the medical device, and wherein the power load is reduced to a level sufficient for the battery to power the hardware component for the predetermined period of time.

Clause 17. The medical device of Clause 15, wherein the medical device comprises a control unit configured to interface with multiple functional units and to control and provide power to a respective functional unit when the functional unit is connected to the control unit, and wherein the instructions, when executed by the one or more processors, further cause the medical device to: determine a battery capacity of a battery powering a the control unit and a plurality of functional units currently connected to the control unit; determine, based on the temperature exceeding the predetermined temperature threshold, that the battery capacity is insufficient to power the plurality of functional units for a predetermined period of time; and disable, responsive to determining that the battery capacity is insufficient, at least one of the plurality of functional units.

Clause 18. The medical device of Clause 15, wherein the medical device comprises a control unit configured to interface with multiple functional units and to control and provide power to a respective functional unit when the functional unit is connected to the control unit, and wherein the instructions, when executed by the one or more processors, further cause the medical device to: determine a battery capacity of a battery powering a the control unit and at least one functional unit currently connected to the control unit; determine, based on the temperature exceeding the predetermined temperature threshold, that the battery capacity is insufficient to power more than the at least one functional unit currently connected to the control unit for a predetermined period of time; and disable, responsive to determining that the battery capacity is insufficient, the control unit's ability to provide power to any additional functional units other than the at least one functional unit currently connected to the control unit.

Clause 19. The medical device of Clause 11, wherein the medical device is a medication dispensing device and the environmental condition comprises a temperature or amount of light, the instructions, when executed by the one or more processors, further cause the medical device to: determine that a medication stored in a compartment of the medication dispensing device has been subjected to the temperature or amount of light for more than a predetermined period of time; and switch the operation mode of the medical device by locking the compartment to prevent a dispense of the medication.

Clause 20. The medical device of Clause 11, wherein the medical device is an infusion device and the environmental condition comprises a temperature or amount of light, the instructions, when executed by the one or more processors, further cause the medical device to: determine that a medication designated for administration by the infusion device to the patient has been subjected to the temperature or amount of light for more than a predetermined period of time; and switch the operation mode of the medical device by electronically disabling a pumping mechanism of the medical device to prevent the medication from being administered to the patient.

Clause 21. A non-transitory machine-readable storage medium embodying instructions that, when executed by a machine, cause the machine to perform operations comprising: monitoring, using one or more sensors, an environmental condition of a physical environment proximate to a medical device; determining a value representative of the environmental condition exceeds a threshold for safe operation of the medical device with regard to care of a patient; and automatically switching, responsive to the value exceeding the threshold, an operation mode of the medical device from a first mode currently programmed for the care of the patient to a second mode, the second mode using different parameters than the first mode to control the medical device.

Further Consideration

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

Features described may include machine learning. Machine learning may include models, equations, artificial neural networks, recurrent neural networks, convolutional neural networks, decision trees, or other machine readable artificial intelligence structure. Examples of machine learning and modeling features which may be included in the embodiments discussed above are described in "A survey of machine learning for big data processing" by Qiu et al. in EURASIP Journal on Advances in Signal Processing (2016) which is hereby incorporated by reference in its entirety.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

As used herein, the terms "real time" "realtime" or "real time" generally signify a time frame for the associated concept. For example, real time processing of an input refers to a process that receives the input and provides a response without observable latency during the process. In contrast, a non-real time processing of the input may include storing the input for assessment at a later time (e.g., according to a schedule).

What is claimed is:

1. A method, comprising:
   monitoring, using one or more sensors, an environmental condition of a physical environment proximate to a medical device;
   determining a value representative of the environmental condition exceeds a threshold for safe operation of the medical device with regard to care of a patient; and
   automatically switching, responsive to the value exceeding the threshold, an operation mode of the medical device from a first mode currently programmed for the care of the patient and that comprises determining an operation performance of a hardware device based on a first sensor measurement to a second mode that comprises disabling use of the first sensor measurement and determining the operation performance based on a software algorithm that does not use the first sensor measurement.

2. The method of claim 1, wherein the medical device comprises an infusion device and the one or more sensors comprises a magnetometer, the environmental condition comprising a magnetic field, and wherein the first sensor measurement is provided by a Hall sensor, and the operation performance is associated with a pumping mechanism administering a fluid to the patient.

3. The method of claim 1, further comprising:
   determining, prior to monitoring the environmental condition, a hardware component of the medical device produced an error exceeding a predetermined error threshold,
   wherein the monitoring of the environmental condition is in response to the error exceeding the predetermined error threshold.

4. The method of claim 1, wherein the environmental condition comprises a temperature, and switching the operation mode of the medical device comprises reducing power to a hardware component of the medical device responsive to the temperature exceeding a predetermined temperature threshold.

5. The method of claim 4, further comprising:
   determining a battery capacity of a battery powering at least the hardware component of the medical device; and
   determining, based on the temperature exceeding the predetermined temperature threshold, that the battery capacity is insufficient to power the hardware component for a predetermined period of time,
   wherein switching the operation mode comprises adjusting operation parameters used to control at least the hardware component to a reduce a power load of the medical device, and
   wherein the power load is reduced to a level sufficient for the battery to power the hardware component for the predetermined period of time.

6. The method of claim 4, wherein the medical device comprises a control unit configured to interface with multiple functional units and to control and provide power to a respective functional unit when the functional unit is connected to the control unit, and wherein the method further comprises:
   determining a battery capacity of a battery powering a the control unit and a plurality of functional units currently connected to the control unit; and
   determining, based on the temperature exceeding the predetermined temperature threshold, that the battery capacity is insufficient to power the plurality of functional units for a predetermined period of time;
   disabling, responsive to determining that the battery capacity is insufficient, at least one of the plurality of functional units.

7. The method of claim 4, wherein the medical device comprises a control unit configured to interface with multiple functional units and to control and provide power to a respective functional unit when the functional unit is connected to the control unit, and wherein the method further comprises:
   determining a battery capacity of a battery powering a the control unit and at least one functional unit currently connected to the control unit;
   determining, based on the temperature exceeding the predetermined temperature threshold, that the battery capacity is insufficient to power more than the at least one functional unit currently connected to the control unit for a predetermined period of time; and
   disabling, responsive to determining that the battery capacity is insufficient, the control unit's ability to provide power to any additional functional units other than the at least one functional unit currently connected to the control unit.

8. The method of claim 1, wherein the medical device is a medication dispensing device and the environmental condition comprises a temperature or amount of light, the method further comprising:
   determining that a medication stored in a compartment of the medication dispensing device has been subjected to the temperature or amount of light for more than a predetermined period of time; and
   switching the operation mode of the medical device by locking the compartment to prevent a dispense of the medication.

9. The method of claim 1, wherein the medical device is an infusion device and the environmental condition comprises a temperature or amount of light, the method further comprising:
   determining that a medication designated for administration by the medication dispensing device to the patient has been subjected to the temperature or amount of light for more than a predetermined period of time; and switching the operation mode of the medical device by electronically disabling a pumping mechanism of the medical device to prevent the medication from being administered to the patient.

10. A medical device, comprising:

one or more processors; and memory including instructions that, when executed by the one or more processors, cause the medical device to:

monitor, using one or more sensors, an environmental condition of a physical environment proximate to the medical device;

determine a value representative of the environmental condition exceeds a threshold for safe operation of the medical device with regard to care of a patient; and automatically switch, responsive to the value exceeding the threshold, an operation mode of the medical device from a first mode currently programmed for the care of the patient and that comprises determining an operation performance of a hardware device based on a first sensor measurement to a second mode that comprises disabling use of the first sensor measurement and determining the operation performance based on a software algorithm that does not use the first sensor measurement.

11. The medical device of claim 10, wherein the medical device comprises an infusion device and the one or more sensors comprises a magnetometer, the environmental condition comprising a magnetic field, and wherein the first sensor measurement is provided by a Hall sensor, and the operation performance is associated with a pumping mechanism administering a fluid to the patient.

12. The medical device of claim 10, wherein the instructions, when executed by the one or more processors, further cause the medical device to:

determine, prior to monitoring the environmental condition, a hardware component of the medical device produced an error exceeding a predetermined error threshold, wherein the monitoring of the environmental condition is in response to the error exceeding the predetermined error threshold.

13. The medical device of claim 10, wherein the environmental condition comprises a temperature, and switching the operation mode of the medical device comprises reducing power to a hardware component of the medical device responsive to the temperature exceeding a predetermined temperature threshold.

14. The medical device of claim 13, wherein the instructions, when executed by the one or more processors, further cause the medical device to:

determine a battery capacity of a battery powering at least the hardware component of the medical device; and determine, based on the temperature exceeding the predetermined temperature threshold, that the battery capacity is insufficient to power the hardware component for a predetermined period of time, wherein switching the operation mode comprises adjusting operation parameters used to control at least the hardware component to a reduce a power load of the medical device, and wherein the power load is reduced to a level sufficient for the battery to power the hardware component for the predetermined period of time.

15. The medical device of claim 13, wherein the medical device comprises a control unit configured to interface with multiple functional units and to control and provide power to a respective functional unit when the functional unit is connected to the control unit, and wherein the instructions, when executed by the one or more processors, further cause the medical device to:

determine a battery capacity of a battery powering a the control unit and a plurality of functional units currently connected to the control unit;

determine, based on the temperature exceeding the predetermined temperature threshold, that the battery capacity is insufficient to power the plurality of functional units for a predetermined period of time; and disable, responsive to determining that the battery capacity is insufficient, at least one of the plurality of functional units.

16. The medical device of claim 13, wherein the medical device comprises a control unit configured to interface with multiple functional units and to control and provide power to a respective functional unit when the functional unit is connected to the control unit, and wherein the instructions, when executed by the one or more processors, further cause the medical device to:

determine a battery capacity of a battery powering a the control unit and at least one functional unit currently connected to the control unit;

determine, based on the temperature exceeding the predetermined temperature threshold, that the battery capacity is insufficient to power more than the at least one functional unit currently connected to the control unit for a predetermined period of time; and disable, responsive to determining that the battery capacity is insufficient, the control unit's ability to provide power to any additional functional units other than the at least one functional unit currently connected to the control unit.

17. The medical device of claim 10, wherein the medical device is a medication dispensing device and the environmental condition comprises a temperature or amount of light, the instructions, when executed by the one or more processors, further cause the medical device to:

determine that a medication stored in a compartment of the medication dispensing device has been subjected to the temperature or amount of light for more than a predetermined period of time; and switch the operation mode of the medical device by locking the compartment to prevent a dispense of the medication.

18. The medical device of claim 10, wherein the medical device is an infusion device and the environmental condition comprises a temperature or amount of light, the instructions, when executed by the one or more processors, further cause the medical device to:

determine that a medication designated for administration by the infusion device to the patient has been subjected to the temperature or amount of light for more than a predetermined period of time; and switch the operation mode of the medical device by electronically disabling a pumping mechanism of the medical device to prevent the medication from being administered to the patient.

19. A non-transitory machine-readable storage medium embodying instructions that, when executed by a machine, cause the machine to perform operations comprising:

monitoring, using one or more sensors, an environmental condition of a physical environment proximate to a medical device;

determining a value representative of the environmental condition exceeds a threshold for safe operation of the medical device with regard to care of a patient; and automatically switching, responsive to the value exceeding the threshold, an operation mode of the medical device from a first mode currently programmed for the care of the patient and that comprises determining an operation performance of a hardware device based on a first sensor measurement to a second mode that comprises disabling use of the first sensor measurement and determining the operation performance based on a software algorithm that does not use the first sensor measurement.

* * * * *